(12) United States Patent
Wainer et al.

(10) Patent No.: US 12,409,307 B2
(45) Date of Patent: Sep. 9, 2025

(54) STRAIN RELIEF ADAPTER FOR MEDICAL TUBING CONNECTION

(71) Applicant: Becton, Dickinson and Company, Franklin Lakes, NJ (US)

(72) Inventors: Jacob Wainer, Natick, MA (US); Richard Bucchianeri, Westford, MA (US); Victor Politis, Natick, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 932 days.

(21) Appl. No.: 17/620,954

(22) PCT Filed: Jun. 21, 2019

(86) PCT No.: PCT/US2019/038571
§ 371 (c)(1),
(2) Date: Dec. 20, 2021

(87) PCT Pub. No.: WO2020/256743
PCT Pub. Date: Dec. 24, 2020

(65) Prior Publication Data
US 2022/0323738 A1    Oct. 13, 2022

(51) Int. Cl.
*A61M 39/10*    (2006.01)
*A61M 25/00*    (2006.01)

(52) U.S. Cl.
CPC ........ *A61M 39/10* (2013.01); *A61M 25/0097* (2013.01); *A61M 2039/1066* (2013.01); *A61M 2039/1077* (2013.01); *A61M 2207/00* (2013.01)

(58) Field of Classification Search
CPC .............. A61M 39/10; A61M 25/0097; A61M 2039/1066; A61M 2039/1077; A61M 2207/00; A61M 39/12; A61M 25/00; A61M 25/06; A61M 2025/0098
See application file for complete search history.

(56) References Cited

U.S. PATENT DOCUMENTS

| 5,257,980 | A | 11/1993 | Van Antwerp et al. |
| 10,143,411 | B2 | 12/2018 | Cabot |
| 2001/0049519 | A1* | 12/2001 | Holman ................. B29C 70/72 604/905 |
| 2005/0137524 | A1 | 6/2005 | Sakai et al. |
| 2010/0283238 | A1 | 11/2010 | Deighan et al. |
| 2016/0339226 | A1 | 11/2016 | Sealfon |
| 2017/0128060 | A1 | 5/2017 | St. Onge et al. |

(Continued)

FOREIGN PATENT DOCUMENTS

| CN | 101119765 A | 2/2008 |
| CN | 212880609 U | 4/2021 |
| EP | 0168239 A1 | 1/1986 |

(Continued)

*Primary Examiner* — Theodore J Stigell
(74) *Attorney, Agent, or Firm* — Dickinson Wright PLLC

(57) ABSTRACT

A strain relief adapter (100) for a medicament delivery device (200) includes a flexible body (101) having a first end (102) configured to connect to one of a fluid connector and a pump connector, a second end (104) configured to connect to tubing, a hollow fluid path (108, 110, 112, 114) therethrough fluidly connecting the first and second ends, and a plurality of external strain relief ridges (106) disposed between the first and second ends.

11 Claims, 5 Drawing Sheets

(56) References Cited

U.S. PATENT DOCUMENTS

2018/0303986 A1    10/2018  Meacham
2019/0030242 A1*    1/2019  Searle ............... A61M 5/14228

FOREIGN PATENT DOCUMENTS

| EP | 0450330 A1 | 10/1991 |
| EP | 3370815 A1 | 9/2018 |
| JP | 2000-271228 A | 10/2000 |
| JP | 2013-005865 A | 1/2013 |
| JP | 2013-066720 A | 4/2013 |
| JP | 2014-087644 A | 5/2014 |
| JP | 2014-515623 A | 7/2014 |
| JP | 2017-506115 A | 3/2017 |
| WO | WO-2011-044217 A1 | 4/2011 |
| WO | WO-2012-002299 A1 | 1/2012 |
| WO | WO-2015-111680 A1 | 7/2015 |
| WO | WO 2018033628 A1 | 2/2018 |
| WO | WO-2018-204636 A2 | 11/2018 |

* cited by examiner

US 12,409,307 B2

STRAIN RELIEF ADAPTER FOR MEDICAL TUBING CONNECTION

CROSS-REFERENCE TO RELATED APPLICATIONS

This application is a U.S. national stage of PCT International Application No. PCT/US2019/038571 filed Jun. 21, 2019.

FIELD OF THE INVENTION

The present invention relates to medical devices, and more particularly, tubing connections in medical devices.

BACKGROUND OF THE INVENTION

Long-term use can lead to cracks in line sets, such as infusion sets, particularly for active patients. Such cracks often occur at joints where tubing connects, for example, to a pump or to a fluid connector. Better protection for joints is desirable.

SUMMARY OF EMBODIMENTS OF THE INVENTION

Accordingly, it is an aspect of the present invention to provide a strain relief adapter for a medicament delivery device.

The foregoing and/or other aspects of the present invention are achieved by providing a strain relief adapter for a medicament delivery device, including: a flexible body having a first end configured to connect to one of a fluid connector and a pump connector, a second end configured to connect to tubing, a hollow fluid path therethrough fluidly connecting the first and second ends, and a plurality of external strain relief ridges disposed between the first and second ends.

The foregoing and/or other aspects of the present invention are also achieved by providing a medicament delivery device, including a fluid connector for connecting to a base having a cannula that is insertable into a patient, tubing, and a flexible strain relief adapter providing a fluid path between the tubing and the fluid connector, and having strain relief ridges disposed on an exterior thereof to provide flexibility in the connection between the tubing and the fluid connector.

The foregoing and/or other aspects of the present invention are also achieved by providing a method of assembling a medicament delivery device, including providing a fluid connector for connecting to a base with a cannula that is insertable into a patient, providing tubing, connecting a first end of a flexible strain relief adapter to the fluid connector, and connecting a second end of the strain relief adapter to the tubing, thereby forming a fluid path from the tubing to the fluid connector.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 2:
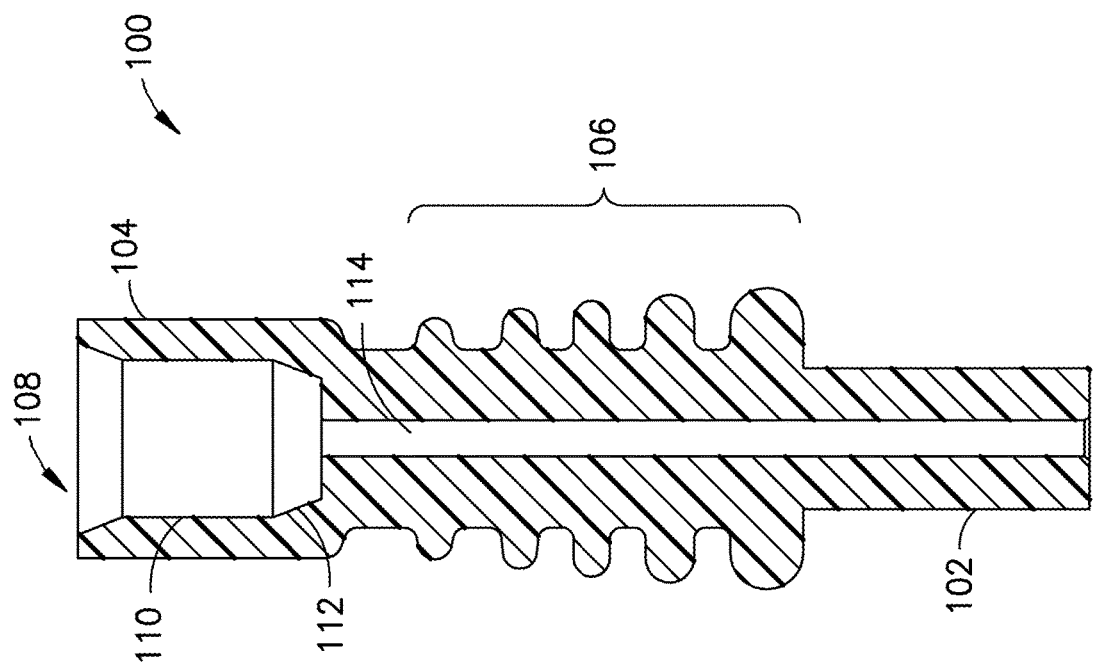
FIG. 2 is a cross-sectional view of the adapter of FIG. 1.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges around and including the given value, for example, general tolerances associated with manufacturing, assembly, and use of the described embodiments.

Figure 1:
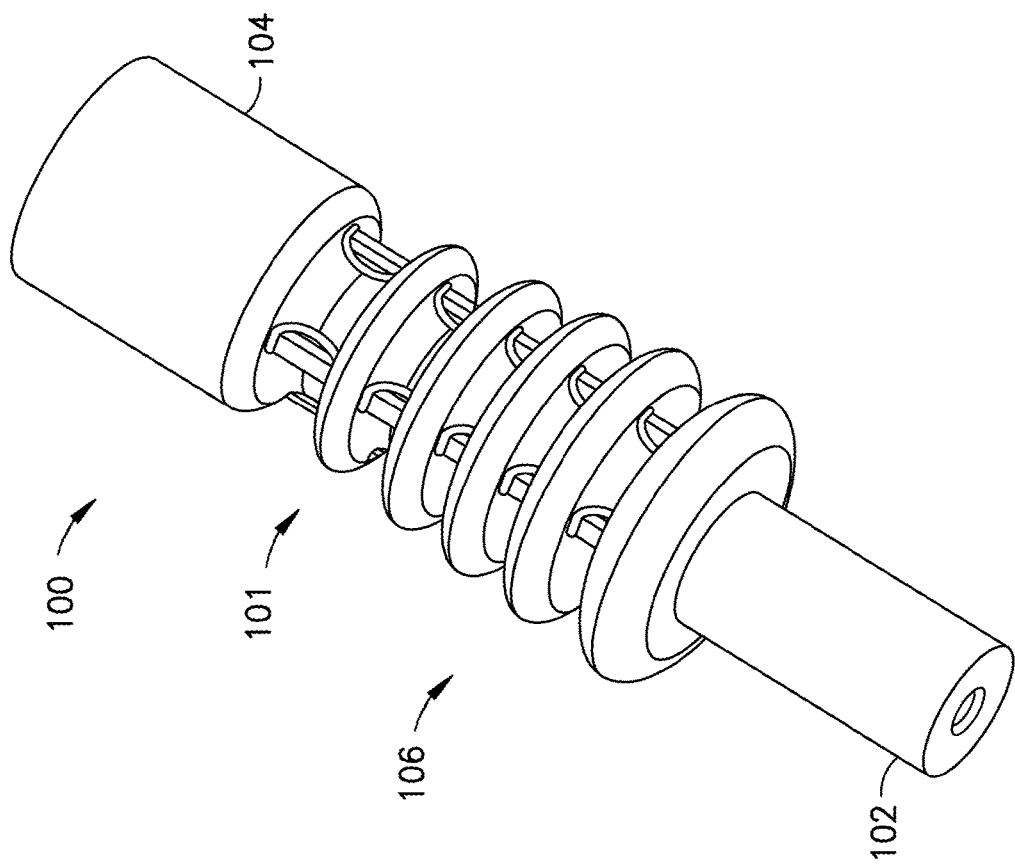
FIG. 1 is a perspective view of a strain relief adapter in accordance with an embodiment of the present invention.

FIG. 1 is a perspective view of a flexible strain relief adapter 100 in accordance with an embodiment of the present invention. The adapter 100 includes a flexible plastic body 101 that has a first end 102 configured to connect with a pump or a fluid connector of a medicament delivery device, and has a second end 104 configured to connect with tubing. As shown in FIGS. 1 and 2, the adapter 100 has a plurality of strain relief ridges 106 axially arrayed on an exterior of the adapter 100.

In accordance with one embodiment, each of the strain relief ridges 106 radially circumscribes the adapter 100. In the embodiment shown in FIGS. 1 and 2, adjacent ones of the strain relief ridges 106 decrease in diameter along a direction from the first end 102 toward the second end 104. Additionally, the strain relief ridges 106 decrease in axial thickness along the direction from the first end 102 toward the second end 104. Further, the strain relief ridges 106 are substantially evenly spaced. One skilled in the art, however, will appreciate that different spacing and/or sizing of the strain relief ridges can be employed without departing from the invention's scope.

As shown in FIG. 2, the second end 104 of the adapter 100 has a first inward taper 108 to aid in receiving an end of the tubing. Axially adjacent to the first inward taper or first tapered portion 108 is a tubing-seating portion 110 and then a second inward taper 112. Adjacent to the second taper 112 is a smaller diameter portion or step down portion 114 that extends all the way to the first end. The step down portion 114, the second inward taper 112, the tubing-seating portion 110, and the first tapered portion 108 form a hollow fluid path extending through the adapter 100.

Figure 3:
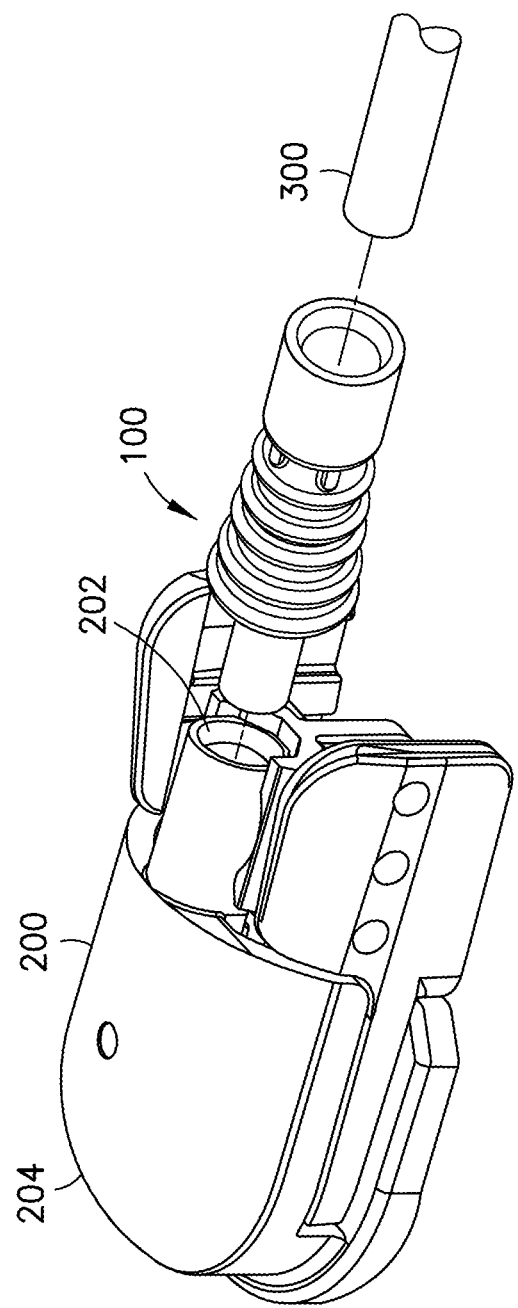
FIG. 3 is a perspective view of assembling the adapter of FIG. 1 with tubing and a fluid connector.
Figure 4:
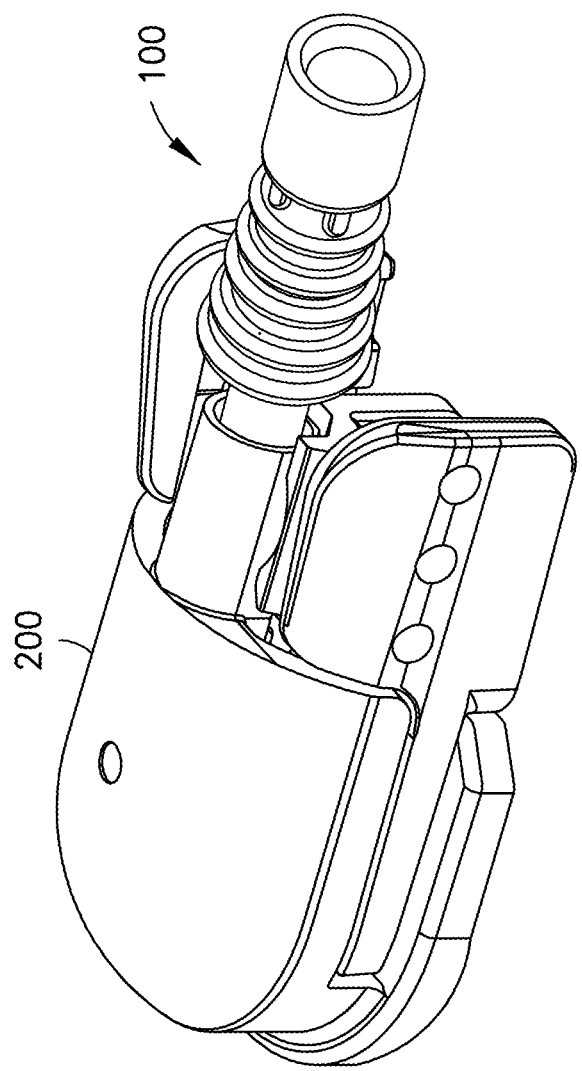
FIG. 4 is a perspective view of the adapter of FIG. 1 connected with the fluid connector of FIG. 3.
Figure 5:
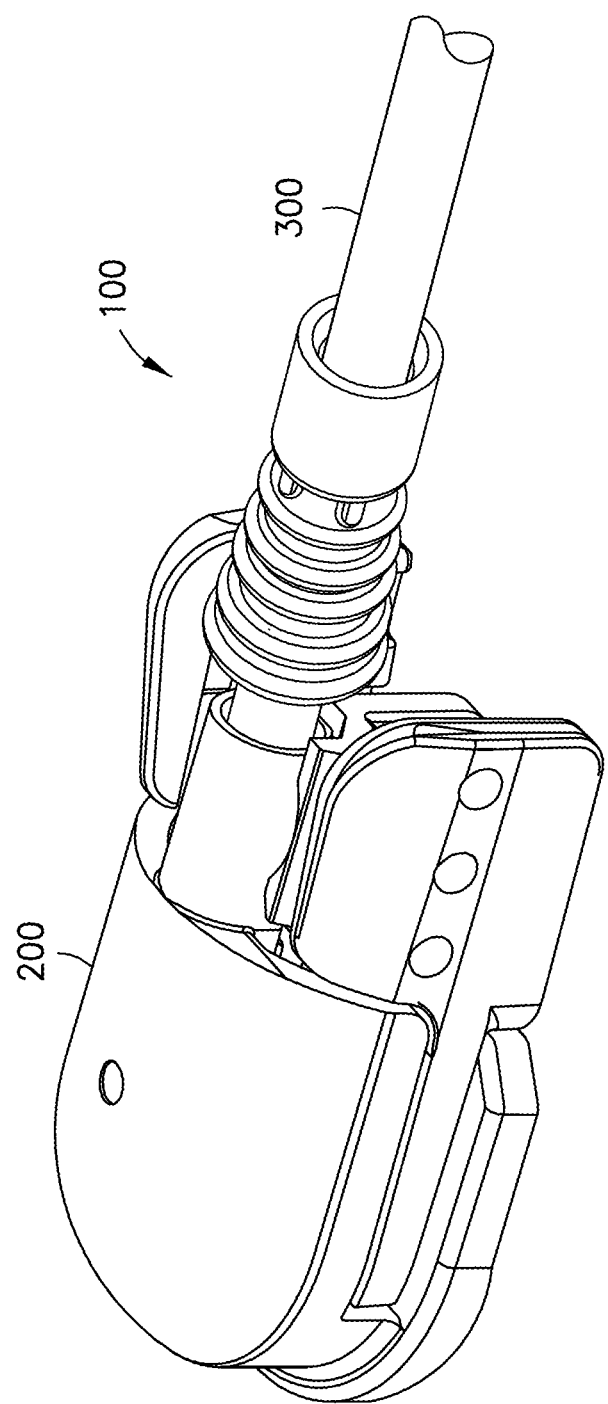
FIG. 5 is a perspective view of the adapter of FIG. 1 connected with the tubing and fluid connector of FIG. 3.

As shown in FIG. 3, the adapter 100 is preferably disposed between a fluid connector 200 and tubing 300. To join the adapter 100 with the fluid connector, according to one embodiment, a friction fit between the first end 102 of the adapter 100 and an opening 202 on the fluid connector provides sufficient interconnection to retain the adapter 100 with the fluid connector 200. According to another embodiment, and assembler dispenses a ring of UV curable adhesive around the first end 102 of the connector and/or in the opening 202 of the fluid connector 200, inserts the first end 102 into the opening 202, and subsequently applies UV light to cure the adhesive.

According to one embodiment, the adapter 100 is translucent or transparent to aid the UV curing. One skilled in the art will appreciate that other adhesives or methods for joining the adapter 100 with another element can be employed without departing from the present invention's scope.

Similar to joining the adapter 100 to the fluid connector 200, an assembler can join the adapter 100 with the tubing 300 using a friction fit or a UV curable adhesive on a first end of the tubing 300 and/or the second end 104 of the adapter.

Similarly, an assembler can connect a second end of the tubing 300 to a second end 104 of a second flexible strain relief adapter 100, and join a first end 102 of the second adapter 100 to a pump connector cap or directly to a pump (not shown) to form a fluid path between the pump and the fluid connector 200.

Figure 6:
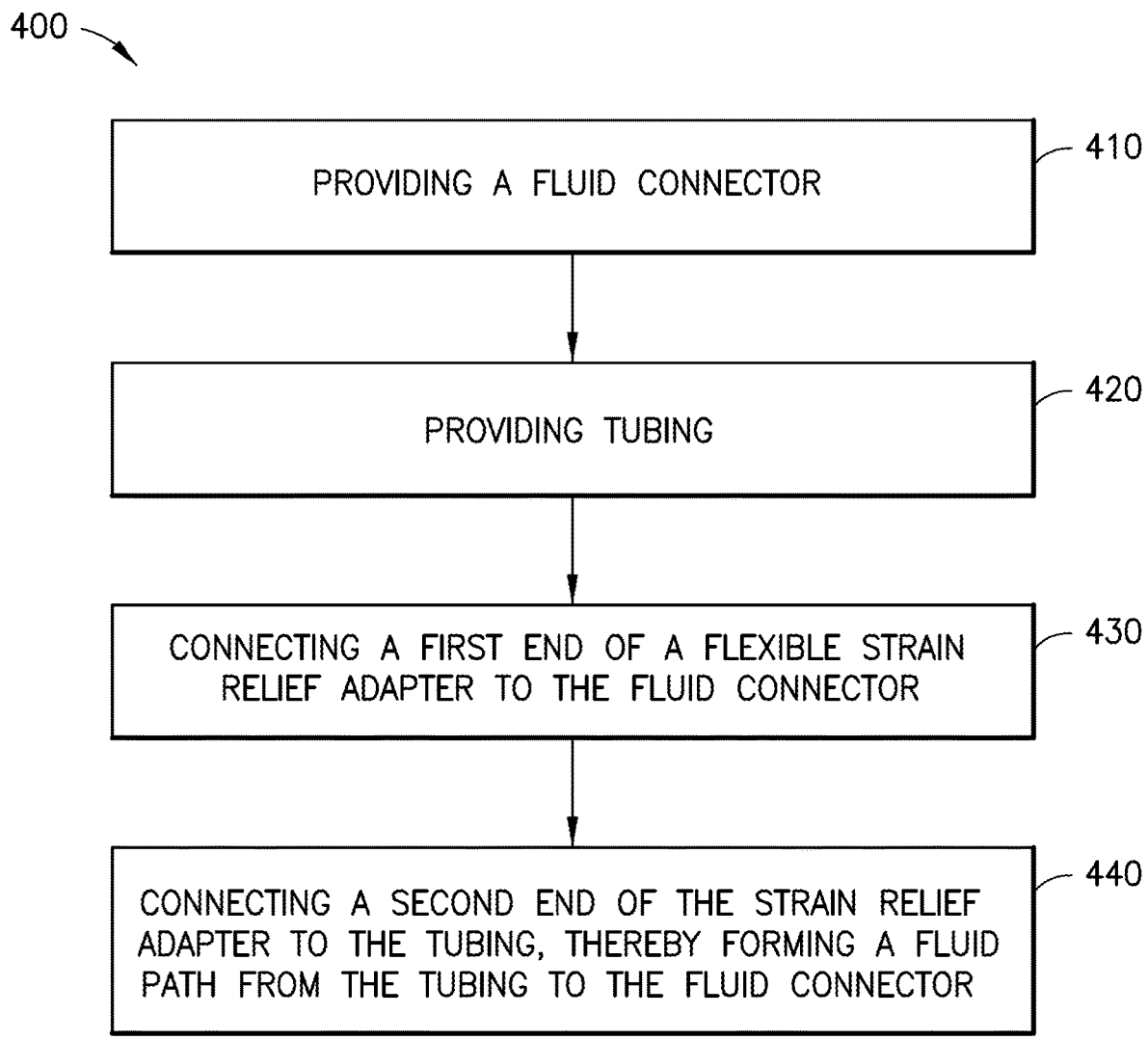
FIG. 6 is a block diagram of a method of assembling a medicament delivery device.

FIG. 6 illustrates a method 400 of assembling a medicament delivery device. In operation 410 and 420, the assembler provides a fluid connector 200 and tubing 300. In operation 430, the assembler connects the first end 102 of the flexible strain relief adapter 100 to the fluid connector 200. And in operation 440, the assembler connects the second end 104 of the adapter 100 to the tubing 300, thereby forming a fluid path from the tubing 300 to the fluid connector 200 through the flexible in-line strain relief adapter 100.

In the previously described embodiments, the adapter 100 has been a separate piece joined to the fluid connector. But the adapter 100 and the fluid connector 200 can be integrally formed as a unitary structure without departing from the invention's scope. According to one embodiment, a manufacturer can form a main body 204 (including the opening 202) of the fluid connector 200 in a first molding shot, and subsequently form the adapter in the opening 202 as a second molding shot. According to one embodiment, the material in the second shot is more flexible that the material in the first molding shot.

Examples of materials that a manufacturer can employ for the first molding shot include acrylonitrile-butadienestyrene (ABS—e.g., Lustran® from Ineos), polycarbonate (PC—e.g., Lexan™ from SABIC), nylon (e.g., Zytel® from DuPont), cyclo olefin polymer (COP—e.g., ZEONEX® and ZEONOR® from Zeon), polyoxymethylene (POM—e.g., Delrin® from DuPont), and polyphenylene sulfide (PPS—e.g., from SABIC). Examples of materials that a manufacturer can employ for the second molding shot include thermoplastic elastomers (TPE), styrenics or olefin based polymers (e.g Medalist® from Teknor Apex or other styrenics or olefin based polymers from Polyone, Dynaflex, OnFlex, and Versaflex), thermal plastic olefin (TPO) based TPE (e.g., ENGAGE™ from Dow), TPE (e.g., from Infuse), and thermoplastic polyurethane (TPU—such as Elastollan® from BASF, or Pellethane® from Lubrizol).

According to yet another embodiment, the manufacturer can form the main body 204 and the adapter 100 in a single molding shot.

Employing embodiments of the present invention can improve the lifespan of tubing joints at fluid/base connections and at reservoir/pump connections. By employing the inventive flexible in-line strain relief adapter at the joints of tubing, the end user or patient can enjoy prolonged use of a product under what would otherwise be joint-fatigued conditions with less chance of line set failure.

Although only a few embodiments of the present invention have been shown and described, the present invention is not limited to the described embodiments. It will be appreciated by those skilled in the art that other changes may also be made to the disclosed embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

Various aspects of the multiple embodiments may be employed independently or in combinations thereof.

The invention claimed is:
1. A medicament delivery device, comprising:
   a fluid connector for connecting to a base having a cannula that is insertable into a patient;
   tubing;
   a pump;
   a first flexible strain relief adapter, comprising a flexible body comprising:
      a first end configured to connect to the fluid connector;
      a second end configured to connect to the tubing;
      a hollow fluid path therethrough fluidly connecting the first and second ends; and
      a plurality of external strain relief ridges disposed between the first and second ends to provide flexibility in the connection between the tubing and the fluid connector; and
   a second flexible strain relief adapter providing a fluid path between the tubing and the pump, and having strain relief ridges disposed on an exterior thereof to provide flexibility in the connection between the tubing and the pump.
2. The medicament delivery device according to claim 1, wherein the fluid path has at least one internal taper between the first and second ends.
3. The medicament delivery device according to claim 2, wherein the fluid path has:
   a first portion extending from the first end and having a first diameter;

a second portion extending from the second end and having a second diameter; and the internal taper disposed between the first and second portions.

4. The medicament delivery device according to claim 1, wherein the fluid path is tapered at the second end to receive the tubing.

5. The medicament delivery device according to claim 1, wherein adjacent ones of the plurality of strain relief ridges increase in diameter along a direction from the second end to the first end.

6. The medicament delivery device according to claim 1, wherein adjacent ones of the plurality of strain relief ridges increase in axial thickness along a direction from the second end to the first end.

7. A method of assembling a medicament delivery device in accordance with claim 1, comprising:

providing the fluid connector;

providing the tubing;

connecting the first end of the first flexible strain relief adapter to the fluid connector;

connecting the second end of the first flexible strain relief adapter to the tubing, thereby forming the fluid path from the tubing to the fluid connector; and connecting the second flexible strain relief adapter between the tubing and the pump to create the fluid path between the pump and the fluid connector.

8. The method according to claim 7, wherein connecting the first end of the first strain relief adapter to the fluid connector comprises friction fitting the first end of the first strain relief adapter into an opening in the fluid connector.

9. The method according to claim 7, wherein connecting the first end of the first strain relief adapter to the fluid connector comprises:

providing a ring of UV curable adhesive on one of the first end of the first strain relief adapter and the fluid connector;

inserting the first end of the first strain relief adapter into an opening in the fluid connector; and applying UV light to cure the ring of adhesive.

10. The method according to claim 9, further comprising:

connecting a second flexible strain relief adapter between the tubing and the pump to create a fluid path between the pump and the fluid connector;

wherein connecting second flexible strain relief adapter between the tubing and a pump comprises:

providing a second ring of UV curable adhesive on one of the pump and an end of the second strain relief adapter;

inserting the end of the second strain relief adapter into an opening in the pump; and applying UV light to cure the second ring of adhesive.

11. A strain relief adapter for a medicament delivery device, comprising a flexible body comprising:

a first end configured to connect to one of a fluid connector and a pump connector;

a second end configured to connect to tubing;

a hollow fluid path therethrough fluidly connecting the first and second ends; and a plurality of external strain relief ridges disposed between the first and second ends, wherein adjacent ones of the plurality of strain relief ridges increase in diameter along a direction from the second end to the first end, wherein the fluid path has:

a first portion extending from the first end and having a first diameter; and a second portion extending from the second end and having a second diameter, wherein the second diameter is larger than the first diameter.

\* \* \* \* \*